United States Patent
Johnsen (10) Patent No.: US 10,123,864 B2
(45) Date of Patent: Nov. 13, 2018

(54) VASCULAR FILTER AND ANCHORING ARRANGEMENT THEREOF

(71) Applicant: COOK MEDICAL TECHNOLOGIES LLC, Bloomington, IN (US)

(72) Inventor: Jeppe Dufresne Johnsen, Froerup (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 191 days.

(21) Appl. No.: 14/755,478

(22) Filed: Jun. 30, 2015

(65) Prior Publication Data
US 2015/0374481 A1    Dec. 31, 2015

(30) Foreign Application Priority Data

Jun. 30, 2014  (GB) .................................. 1411590.1
May 11, 2015  (EP) .................................. 15275133

(51) Int. Cl.
*A61F 2/01*      (2006.01)
*A61F 2/848*   (2013.01)

(52) U.S. Cl.
CPC ............... *A61F 2/01* (2013.01); *A61F 2/848* (2013.01); *A61F 2002/016* (2013.01); *A61F 2002/8483* (2013.01); *A61F 2210/0004* (2013.01); *A61F 2220/0016* (2013.01)

(58) Field of Classification Search
CPC . A61F 2/01; A61F 2002/016; A61F 2002/018
See application file for complete search history.

(56) References Cited

U.S. PATENT DOCUMENTS

| | | |
|---|---|---|
| 4,957,501 A | 9/1990 | Lahille et al. |
| 7,857,845 B2 | 12/2010 | Stacchino et al. |
| 8,092,484 B2 | 1/2012 | Kashkarov et al. |
| 8,162,970 B2 | 4/2012 | Gilson et al. |
| 8,235,047 B2 | 8/2012 | Swann et al. |
| 8,444,688 B2 | 5/2013 | Sherry |

(Continued)

FOREIGN PATENT DOCUMENTS

| | | |
|---|---|---|
| WO | WO 2007/079413 A2 | 7/2007 |
| WO | WO 2010/033725 A2 | 3/2010 |

(Continued)

OTHER PUBLICATIONS

Extended European Search Report for EP Application No. 15275133, dated Nov. 2, 2015.

*Primary Examiner* — Tuan V Nguyen
(74) *Attorney, Agent, or Firm* — Brinks Gilson & Lione (57) ABSTRACT

A vena cava filter includes a plurality of filter legs with distal ends. Each distal end is a tip which curves radially outwardly and ends in a spherical or part spherical enlarged head element. A biodegradable barb is attached to the enlarged head element and is made of a biodegrade material, such that after degradation the enlarged head element also is left embedded in the vessel wall. The degradation of the barb will prevent further penetration of the distal end of the filter legs into the vessel wall and avoid any risk of piercing through the vessel wall. The enlarged head element also ensures that the distal ends of the filter legs remain firmly attached into the vessel wall in order to ensure correct long term placement of the filter in the vessel.

19 Claims, 5 Drawing Sheets

(56) References Cited

U.S. PATENT DOCUMENTS

| | | | |
|---|---|---|---|
| 2001/0039431 A1* | 11/2001 | DeVries | A61F 2/01 606/200 |
| 2002/0103501 A1* | 8/2002 | Diaz | A61F 2/01 606/200 |
| 2003/0040771 A1 | 2/2003 | Hyodoh et al. | |
| 2005/0159771 A1* | 7/2005 | Petersen | A61F 2/01 606/200 |
| 2006/0025852 A1 | 2/2006 | Armstrong et al. | |
| 2006/0078740 A1 | 4/2006 | Zern et al. | |
| 2006/0095068 A1 | 5/2006 | WasDyke et al. | |
| 2007/0112373 A1* | 5/2007 | Carr, Jr. | A61F 2/01 606/200 |
| 2007/0227544 A1 | 10/2007 | Swann et al. | |
| 2008/0027481 A1* | 1/2008 | Gilson | A61F 2/01 606/200 |
| 2008/0188887 A1 | 8/2008 | Batiste | |
| 2009/0306703 A1* | 12/2009 | Kashkarov | A61F 2/01 606/200 |
| 2010/0030253 A1 | 2/2010 | Harris et al. | |
| 2010/0121373 A1* | 5/2010 | Tekulve | A61F 2/01 606/200 |
| 2011/0276091 A1 | 11/2011 | Melanson et al. | |
| 2012/0221040 A1 | 8/2012 | Eggers | |
| 2012/0245619 A1 | 9/2012 | Guest et al. | |
| 2012/0283811 A1 | 11/2012 | Neilan | |
| 2013/0006294 A1 | 1/2013 | Kashkarov et al. | |
| 2013/0073029 A1 | 3/2013 | Shaw | |

FOREIGN PATENT DOCUMENTS

| | | |
|---|---|---|
| WO | WO 2010/126889 | 11/2010 |
| WO | WO 2011/088090 A1 | 7/2011 |

\* cited by examiner

VASCULAR FILTER AND ANCHORING ARRANGEMENT THEREOF

CROSS-REFERENCE TO RELATED APPLICATIONS

This application claims the benefit of priority under 35 U.S.C. § 119(a) to European Patent Application No. EP 15275133.5, filed May 11, 2015, and to Great Britain Patent Application No. GB 1411590.1, filed Jun. 30, 2014, which are hereby incorporated by reference in their entirety.

TECHNICAL FIELD

The present invention relates to an implantable medical device and in the preferred embodiments to an improved vascular filter and anchoring arrangement for such a filter.

BACKGROUND ART

There are various types and designs of vena cava filters, each having particular advantages and disadvantages. Generally, it is desirable to have a filter design which is able to be deployed endoluminally into a vessel via the jugular or femoral vein by means of the well-known Seldinger technique. The filter is carried on an introducer assembly in a radially compressed condition and once positioned at the desired location it is released and allowed to expand until it engages the walls of the vessel. It is often also desirable to remove the filter after a period of treatment, in which case the filter is designed such that it can be compressed back to its radially contracted configuration and retrieved endoluminally, normally into a sheath of the retrieval assembly. The filter is typically removed via the jugular or femoral vein.

It is important for vena cava and other filters to remain reliably in position for the duration of the period in which they are left in the patient. In particular, the filter must remain in the correct orientation and also must not migrate from the site at which is it first placed. For this purpose, filters are generally provided with filter arms or legs which spring radially outwardly to press against the vessel wall. The extremities of the legs are either sharp or have specific anchor elements which pierce into the vessel wall.

An advantageous design of filter has a conical or part-conical frame provided with a plurality of radially disposed legs coupled to one another at a closed end, or hub, of the frame. Such a filter can provide reliable filtration, can be compressed to a very small diameter for ease of delivery and can minimise the amount of foreign material implanted into the patient.

A problem which can occur with filter assemblies, and which may also be experienced with other types of implantable medical device such as stents, stent grafts, and occlusion devices, is that as a result of the opening force generated by the device struts or legs and the natural movement of the vessel, the anchoring elements can become progressively further embedded into the vessel wall and eventually may pierce through the entire thickness of the vessel. This effect could be expressed as ratcheting of the filter legs and is described in further detail below.

Examples of implantable medical devices including filters can be found in US-2012/0283811, US-2009/0306703, US-2008/0027481 and US-2013/0006294.

DISCLOSURE OF THE INVENTION

The present invention seeks to provide an improved implantable medical device and in the preferred embodiments to an improved vascular filter and anchoring arrangement therefor.

According to an aspect of the present invention, there is provided an implantable medical device including a frame, the frame including at least one leg element having a vessel engaging end and an anchoring element at said end; wherein the anchoring element includes a bulbous element and a barb member extending from the bulbous element; wherein the barb member is made of biodegradable material.

This structure of leg extremity provides a restraining member, namely the bulbous element, which restrains the barb of the leg from penetrating too deeply into the vessel wall.

In an embodiment the bulbous element is generally spherical or part-spherical. It has been found that such a shape is optimal for restraining the leg extremity in the vessel wall and in some instances can also facilitate endothelialisation of the leg extremity. This characteristic assists in retaining the leg extremity in position relative to the vessel wall.

The biodegradable nature of the barb member can provide a significant advantage in that the barb, that is the piercing element, is not a permanent component of the device and once it has degraded the device is preferably left with no other vessel piercing member. The bulbous element, which can become fixed into the vessel wall by the previous piercing action of the anchor element, will act to hold the leg and therefore the device in place in the vessel. For this purpose, it will be appreciated that the bulbous element preferably has a greater diameter than the diameter of the leg, so as to become trapped in the vessel wall both against further progression into the vessel wall and against retraction from the vessel wall.

In an embodiment, the barb element has an elongate needle shape. In this embodiment, the barb may be biodegradable or non-degradable.

Advantageously, the barb element may have a tapering shape.

In an embodiment, the barb element extends in a radially outward direction from the vessel engaging end of the leg. The barb element may extend in a direction rearward relative to a direction of the at least one leg.

In some embodiments, the barb element extends over the bulbous element.

The bulbous element may include a barb fixation recess, the barb including a protrusion extending into the fixation recess.

Preferably, the barb element includes a base portion having a diameter substantially the same as or greater than a maximum diameter of the bulbous element.

In a practical embodiment, the implantable medical includes a plurality of leg elements disposed in spaced relation to one another and extending to radially outward positions.

The device may be a vascular filter such as a vena cava filter.

According to another aspect of the present invention, there is provided an anchoring member for an implantable medical device including a bulbous element and a barb member extending from the bulbous element.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

The accompanying drawings are schematic only. It is to be understood that the dimensions and proportions of the various components of the devices shown in the drawings are not to scale or in proportion relative to one another. It is also to be understood that the drawings depict only the principal components of the device shown therein and that other elements and components of the device which are not central to understanding the teachings herein have been omitted for the sake of clarity.

Figure 1A:
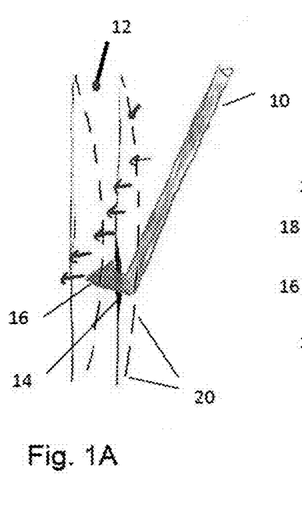
FIGS. 1A to 1C are schematic diagrams showing a leg of a vena cava filter against a vessel wall and depicting how the leg progressively penetrates through the vessel wall during movement thereof.
Figures 1B, 1C:
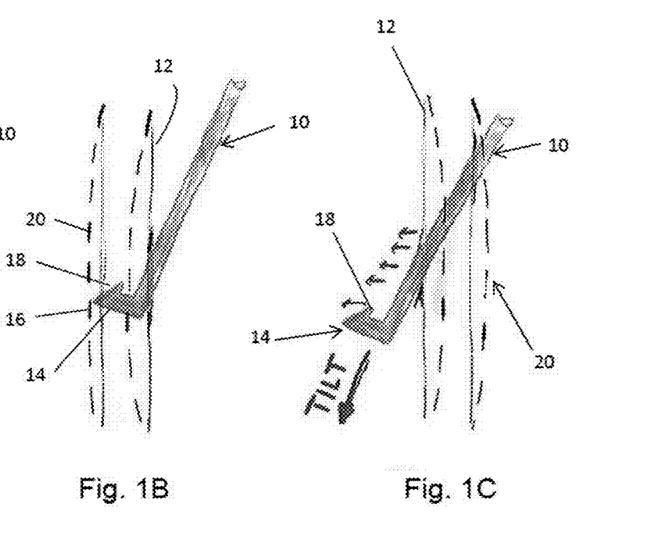

Referring first to FIGS. 1A to 1C, these show an example of conventional filter arrangement and specifically a filter leg 10 of such a filter and a part of the vena cava wall 12. A person skilled in the art will appreciate that a filter of such a nature will have a plurality of filter legs 10 which extend radially outwardly from a central hub in a generally conical arrangement. The filter legs 10 are typically spaced circumferentially so as to contact the vena cava wall 12 at spaced positions around the vessel wall.

At the extremity of each filter leg 10 there is provided an anchor element 14, which is shown schematically as being a section of the leg wire angled by approximately 90° to the main portion of the leg 10. The anchor element 14 includes a sharp extremity or barb 16 designed to pierce into the vessel wall 12, and a rearwardly extending hook 18 which in practice ensures that the anchor element 14 cannot be pulled back out of the vessel wall.

With reference to FIG. 1A, the vessel wall 12 is shown in continuous lines in what could be described as its normal at rest condition. The anchor element 14 can be seen having pierced into the vessel wall 12 to hold the end of the filter leg 10 to the vena cava wall and therefore to hold the filter in position. The dotted line 20 in FIG. 1A depicts the movement of the vessel wall 12, which can be expected to occur during normal conditions, for example as a result of changes in blood pressure caused by normal heart function. In FIG. 1A, the vessel wall 12 is shown moving inwardly and thus towards the filter assembly, whereas in FIG. 1B the dotted line 20 shows the wall extending outwardly of the centre of the vessel and therefore away from the filter. Again, in FIG. 1C the dotted line 20 shows the vessel wall moving inwardly again, towards the centre of the vessel.

As will be apparent from FIG. 1A, when the vessel wall 12 moves inwardly as shown by the dotted lines 20, the anchor element 14 of the strut 10 will tend to be pressed further into the wall 12 by virtue of the sharp point 16. As depicted in FIG. 1B, when the vena cava wall 12 expands outwardly, as shown by the dotted lines 20 in FIG. 1B, the anchor element 14 will be carried with the expanding vessel wall due to the provision of the rearwardly extending hook 18. Further inward and outward movement of the vena cava wall 12 over time will cause the anchor element to move progressively further into the thickness of the vessel wall 12 and eventually, as shown in FIG. 1C, it will pierce through the vessel wall. Not only will this pierce the wall 12 itself but can also cause the filter to tilt within the vessel, particularly when only some of the filter struts 10 pierce through the vessel wall, which can occur as the result of differential movement of the vessel wall 12.

Figure 2A:
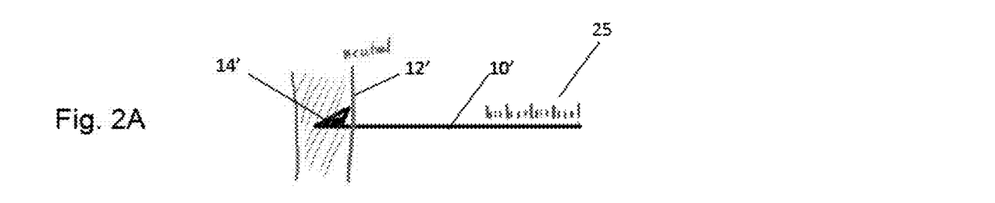
FIGS. 2A to 2C are additional schematic diagrams depicting the ratcheting process which can occur with prior art filter designs.
Figure 2B:
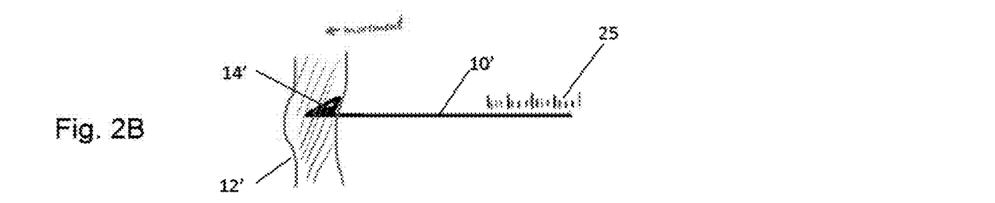
Figure 2C:
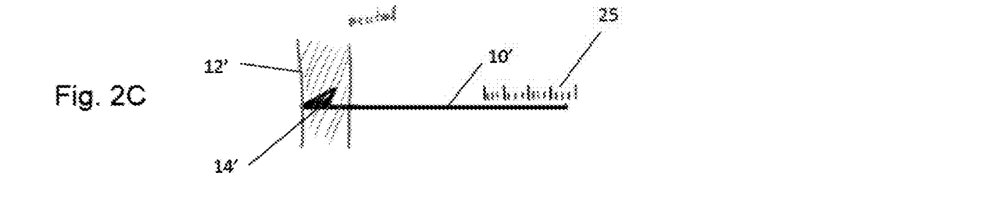

Referring now to FIGS. 2A to 2C, these depict in schematic form what occurs in practice with the filter leg arrangement shown in FIGS. 1A to 1C. As can be seen in FIG. 2A, the filter leg 10' is attached to the vessel 12' by means of the anchor element 14' in what could be described as the normal position. With reference to FIG. 2B, with natural outward movement of the vessel 12', the anchor element 14' is pulled with the vessel wall, yet when the vessel wall 12' returns back to its normal or neutral position, the anchor element 14' moves further into the depth of the vessel wall 12' until it will eventually pass all the way through the thickness of the wall 12'. This effect could be described as ratcheting of the filter leg into the vessel wall. This ratcheting or progressive movement into the vessel wall 12' is represented by the scale markings 25 in FIGS. 2A to 2C. The problem arises as a result of the need to have a sharp point to the anchor element and also a mechanism to prevent the anchor element from being withdrawn from the vessel wall.

Figure 3:
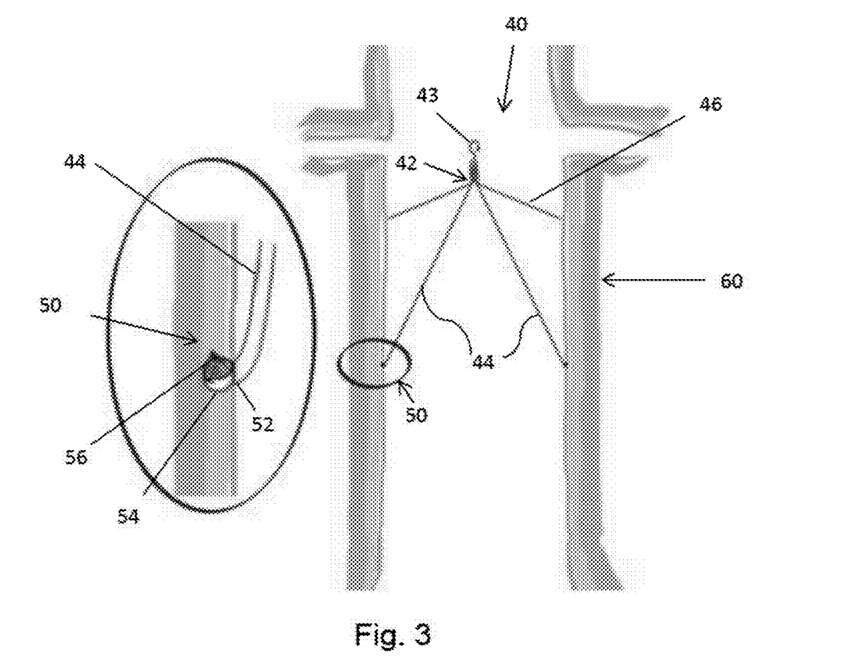
FIG. 3 is a schematic diagram of an embodiment of vena cava filter according to the teachings herein.

Referring now to FIG. 3, this shows in schematic form an embodiment of vascular filter 40, fitted into a vena cava 60. It is to be understood that although reference is made to the vena cava, the filters and anchoring elements taught herein are suitable for use in all other vessels of the body.

The filter 40 has a generally conical form with a central hub 42 provided, in this example, with a retrieval hook 43 of known type. The hub 42 may have a lumen passing therethrough to enable the filter 40 to be delivered over the wire. In such a case, the lumen in the hub 40 may be provided with a valve or thrombogenic fibres for closing the lumen to the passage of blood.

The filter 40 has a plurality of filter legs, or struts, 44 which extend from the hub 42 outwardly in radial manner, giving the filter 40 a generally conical shape as depicted in FIG. 3. The filter 40 also includes a second set of shorter legs, or struts, 46, which similarly extend radially outwardly from the hub 42 and contact the vessel wall at a location longitudinally spaced from the legs 44, thereby to give the filter 40 two sets of vessel contact points useful in maintaining the orientation of the filter in the vessel 60. The legs 44, 46 are typically wires of round cross-section.

The conical shape of the filter 40 not only provides good filtering characteristics but also facilitates removal of the filter after use, typically by pulling this into a retrieval sheath via the hook 43.

The magnified section in FIG. 3 shows in better detail the distal, or vessel engaging, end 50 of one of the legs 44. As can be seen, at the distal end 50 the leg 44 has a radially outwardly curved tip 52, which in practice will point into the vessel wall. At the tip 52 there is provided a bulbous element 54, hereinafter referred to as an enlarged head element. The head element 54 is, in this embodiment, spherical and has a diameter greater than the diameter of the leg 44, thereby providing a surface or shoulder 58 between itself and the leg 44, best seen in FIG. 4 onwards.

In this embodiment, attached to the enlarged head element 54 is a barb 56 which extends generally in a proximal direction, that is towards the hub 42 and substantially parallel to the vessel wall.

In the example shown in FIG. 3, the barb 56 has a sharp tip and a widening base which ends with a diameter generally as great as the diameter of the enlarged head element 54. The sharp tip of the barb 54 causes the barb, under the pressure of the leg 44, to pierce into the vessel wall, as shown in FIG. 3.

Figure 4:
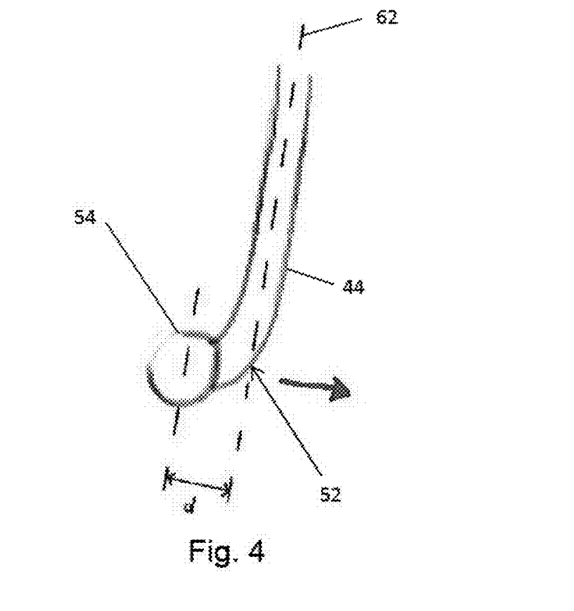
FIG. 4 is an enlarged view of a filter leg extremity of the filter of FIG. 3, after a degradation period.

With reference now to FIG. 4, this shows in enlarged form one of the filter legs 44 and enlarged head element 54. The barb 56 is not shown in this Figure. As will be apparent from FIG. 5, the curved portion 52 of the leg 44 causes the enlarged head 54 to be spaced from the longitudinal axis 62 of the leg 44 by a distance d. In practice, this shape of leg end will enable the curved tip 52 to penetrate into the wall of the vessel 60 until the main, straight portion, of the leg 44 comes into abutment with the vessel wall, with thereafter any further penetration of the leg into the vessel wall being limited as a result of the side-on disposition of the major portion of the leg 44. The distance d is chosen to be equivalent to a part only of the thickness of the vessel wall 60 into which the filter 40 is to be implanted, thereby to ensure that once the outwardly curved tip 52 has become embedded in the vessel wall, this part of the leg 44 will not penetrate through the entire thickness of the vessel wall.

FIG. 4 can also be said to depict the filter leg 44 after a degradation period in which the barb 50 has degraded to leave the enlarged head 54 fully exposed and with the piercing element effectively removed.

Each leg 44 of the filter 40 has in this embodiment a distal leg arrangement of the type shown in the drawings and in particular from FIG. 3 onwards. The shorter filter legs 46 of the second set may in some embodiments also be provided with anchor elements and outwardly curved distal ends of the type shown in connection with the legs 44.

Figure 5:
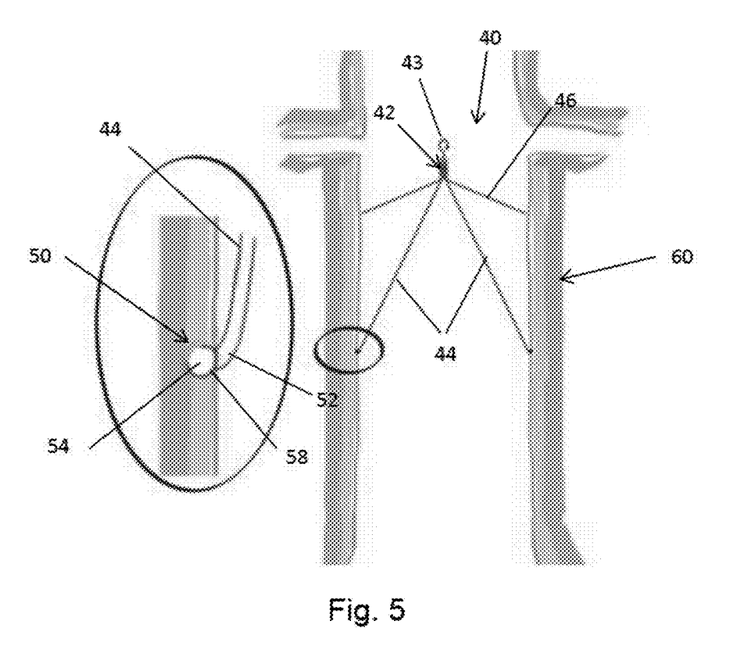
FIG. 5 shows the filter of FIG. 3 after degradation of barbs elements thereof.

Referring now to FIG. 5, this shows the filter 40 of FIG. 3 some time after first deployment and specifically after a specified degradation period. The barbs 56 shown in FIG. 3 are made of a biodegradable material, for example a biodegradable polymer, such as PLA, PGA or PHA, a magnesium or iron based material, or other suitable material. As a result, and as shown in particular in FIG. 5, the barbs will degrade in the vessel over a degradation period determined by the material and structure of the barbs. Once degraded, the distal ends 50 of the of the filter legs 44 will consist solely of the enlarged head elements 54. As the latter elements 54 have no pointed or piercing characteristic, they will not penetrate further into the vessel wall 60 and therefore will not exhibit the ratcheting effect which can be experienced with prior art filter structures. The rearwardly facing shoulder 58 of the enlarged head 54, provided by the greater diameter of the enlarged head 54 compared to the diameter of the filter leg 44, will cause the distal end 50 of the filter leg 44 to remain embedded, or trapped, within the vessel wall, thus ensuring good retention of the filter 14 in the vessel.

Figure 6:
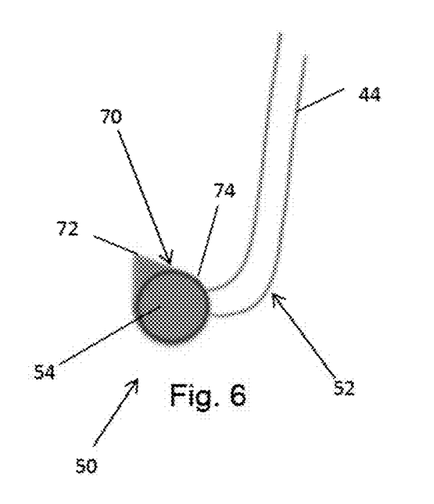
FIG. 6 shows an embodiment of biodegradable barb structure for the filter of FIGS. 4 to 6.

FIGS. 6 to 8C show different designs of enlarged head element 54 and barb for the filter 40. Referring first to FIG. 6, this shows a leg 44 of a filter 40 having at its distal end 50 a barb 70 which envelopes the entirety of the enlarged head element 54. The enlarged head element 54 is in this embodiment spherical. As can be seen in FIG. 6, the barb 70 has a pointed tip 72 and widens to a base 74 just slightly larger in diameter than the diameter of the spherical head element 54. The barb 70 will degrade over time to leave the spherical enlarged head element 54 within the vessel wall 60.

Figure 7:
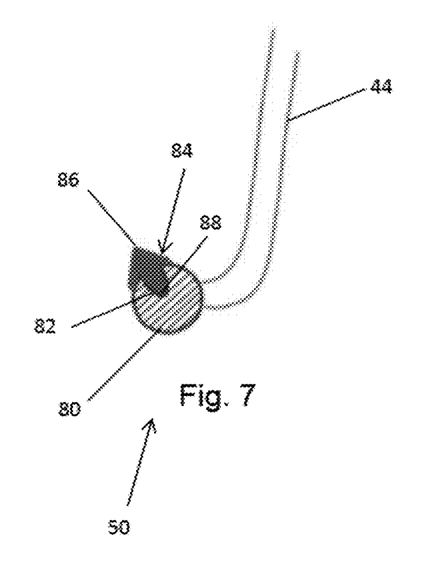
FIG. 7 shows another embodiment of biodegradable barb structure for the filter of FIGS. 4 to 6.

With reference to FIG. 7, this shows a leg 44 of a filter 40 having at its distal end 50 a generally spherical enlarged head element 80 having a tapering recess 82 therein. The recess 82 is preferably round in plan view, but could be of other shapes. The barb 84 includes a tip 86 and a male connector 88 shaped and sized to fit into the recess 82. The barb 84 widens from its sharp tip 86 to its base. The barb is preferably circular in plan view. In this embodiment, the base of the barb 84 is not as wide as the diameter of the enlarged head element 80 but is sufficiently wide to provide a smooth widening surface from the tip 86 of the barb 84 to the widest portion of the enlarged head element 80.

The barb 84 could be attached to the enlarged head 80 by a friction fit or by bonding, for example.

In both embodiments of FIGS. 6 and 7 the barb 70, 80 extends both in radially outward and in a proximal direction, for example at an angle to around 45 degrees to the longitudinal direction of the filter 40 and in practice of the vessel.

Figure 8A:
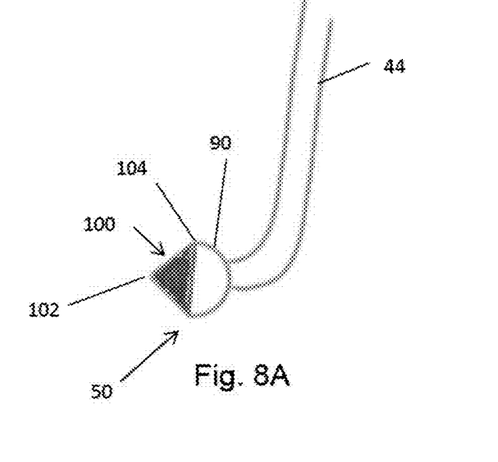
FIGS. 8A to 8C show another embodiment of biodegradable barb structure for the filter of FIGS. 4 to 6.
Figure 8B:
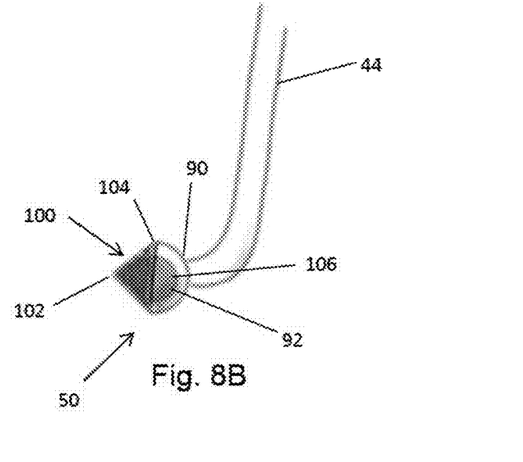
Figure 8C:
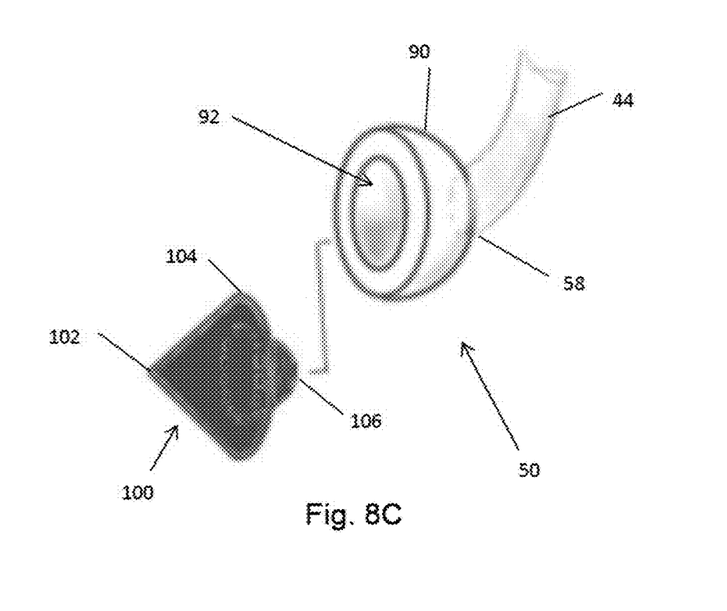

FIGS. 8A to 8C show another embodiment of anchor element for a filter 40 of the type shown in FIGS. 3, 4 and 5. In this embodiment, the enlarged head element 90 is semi-spherical and has a semi-spherical recess 92 therein. A barb member 100 has a pointed tip 102 and widens in conical manner towards a base 104, which has a diameter substantially the same as the maximum diameter of the part-spherical head element 90. The barb element 100 also includes a semi-spherical male coupling element 106 at its base, which is sized to fit within the semi-spherical recess 92 of the head element 90. The barb element 100 is preferably made of a biodegradable material which, after its degradation, will leave the semi spherical head element 90 embedded within the vessel wall. It will be appreciated that in this embodiment, as with the previous embodiments, once the barb element has degraded there will remain in the vessel a blunt retention element 90.

In the embodiment of FIGS. 8A to 8C the barb 100 extends both in a radially outward, at an angle of around 90 degrees to the longitudinal direction of the filter 40 and in practice of the vessel.

Figure 9:
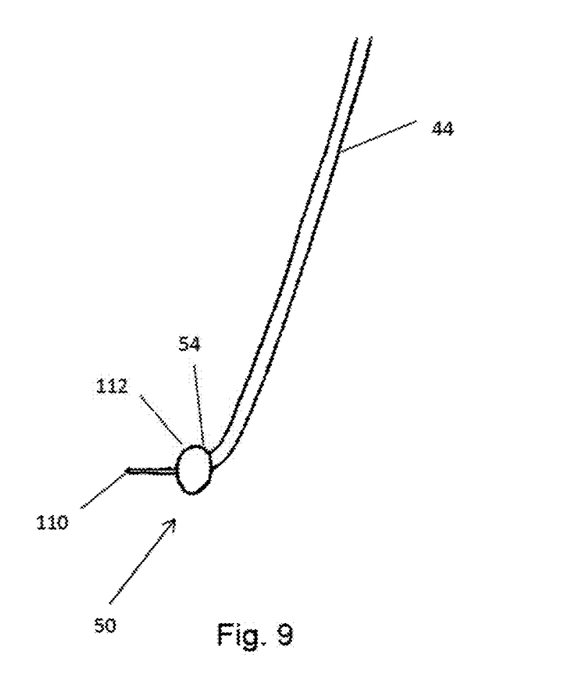
FIG. 9 shows another embodiment of barb structure for the filter of FIGS. 4 to 6.

Referring now to FIG. 9, this shows another embodiment of leg 44 for a filter 40 of the type shown in FIG. 3. In this embodiment, the leg 44 has a distal end with a spherical enlarged head end 54 as with the embodiments of FIGS. 3 to 6, but has a barb 110 which is in the form of a sharp needle extending from the enlarged head 54. The needle 110 is shown extending in a radial direction of a filter leg 44, in which case the needle 110, including the distance d depicted in FIG. 5 provided by the outwardly curving the distal end 50 of the leg 44 is less than the overall thickness of the vessel wall 60. In other embodiments, the needle 110, instead of pointing radially outwardly, may point also in a distal direction, that is towards the hub 42 of the filter 40, in a manner similar to the barbs shown in FIGS. 3, 6 and 7.

In this embodiment, the needle 110 will be sufficiently sharp to pierce into the vessel wall, with the pressure produced by the filter legs 44 and the effect of endothelialisation causing the enlarged head 54 to become embedded into the vessel wall.

The needle 110 may be formed of a substantially non-biodegradable material, for example of a material similar to that of the major portion of the filter 40, in which case the needle will not degrade in the manner described above with respect to the embodiments of FIGS. 3 to 8. The blunt front end of the head element 54 will reduce the effect of ratcheting of the distal end 50 of the filter leg 44 into the vessel wall. It is not excluded, though, that the needle 110 could be made of a biodegradable material as per the embodiments of FIGS. 3 to 8.

In the embodiments described, the enlarged head elements 54 may have a diameter of around 1 mm and the filter legs 44 a diameter in the region of 0.3 to 0.4 mm.

Typically, the distal ends 50 of the filter legs 44 will become ingrown within the wall 60 of the vessel within a period of about 4 weeks or so, in which case the barbs are preferably chosen to degrade within a period of 1 to 3 months following deployment of the filter 40 into the patient's vessel.

In the preferred embodiments, the anchor elements at the distal ends 50 of the legs 44 have no rearwardly extending hook element of a type equivalent to a fishing hook, which again will reduce the risk of ratcheting of the filter.

The filter legs 40 may be made of conventional materials, typically spring materials and/or shape memory materials. Examples include elgiloy, nickel titanium alloy such as Nitinol, cobalt chromium and so on.

Although the filter legs 44, 46 are described as being wires, they could equally be laser cut from a tube.

It is not necessary for the enlarged head elements to be spherical or part-spherical as they could have a variety of other shapes, for instance oval or the like. A person skilled in the art will be able to devise other suitable shapes for these elements.

The barb elements may be formed as one piece with the filer legs 44 or alternatively may be securely joined to the filter legs, for example by adhesive bonding, welding, friction fit, a mechanical coupling or the like.

The barbs may point radially outwardly, that is in a direction normal to the direction of the vessel, while in other embodiments may point towards the hub end of the filter. It is to be appreciated that the barbs may be at any angle between these two points, that is to point partially outwardly and partially proximally towards the hub. It is preferred that the barbs do not extend in a forward direction (away from the hub 40), although this is not excluded.

Although in the preferred embodiments described above every filter leg 44 has the form shown, that is with a bulbous element and barb, it is not excluded that in some embodiments only some of the legs 44 may have distal ends of this type, in which case legs without anchor elements may simply have straight distal ends.

Although the embodiments described above relate to a filter, the teachings herein are applicable to other implantable medical devices including but not limited to: occlusion devices, stents, stent grafts, embolization devices and the like.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosures in the abstract accompanying this application and in British patent application number 1411590.1, from which this European patent application claims priority, are incorporated herein by reference.

The invention claimed is:

1. An implantable medical device including a frame, the frame including at least one leg element having a vessel engaging end and an anchoring element at said end; wherein the anchoring element includes a bulbous element and a barb member extending from the bulbous element, wherein the barb member attached to the bulbous element; wherein the bulbous element and the barb member configured to embed within the vessel wall; wherein the barb member is made of biodegradable material, wherein the bulbous element is in the form of an enlarged head, wherein the enlarged head has a fixed size and shape and does not degrade, wherein after the barb member fully degrades, the vessel engaging end will consist solely of the enlarged head portion, and wherein the barb member is biodegradable so as to leave the bulbous element exposed within the vessel wall.

2. An implantable medical device according to claim 1, wherein the bulbous element is spherical or part-spherical.

3. An implantable medical device according to claim 1, wherein the barb member has an elongate needle shape.

4. An implantable medical device according to claim 1, wherein the barb member has a tapering shape or portion.

5. An implantable medical device according to claim 1, wherein the barb member extends in a radially outward direction relative to a longitudinal direction of the medical device.

6. An implantable medical device according to claim 1, wherein the at least one leg extends from the barb member in a first direction; wherein the barb member extends in a direction opposite to the first direction of the at least one leg.

7. An implantable medical device according to claim 1, wherein the barb member extends over the bulbous element.

8. An implantable medical device according to claim 1, wherein the bulbous element includes a barb fixation recess, the barb member including a protrusion extending into the fixation recess.

9. An implantable medical device according to claim 1, wherein the barb member includes a base portion having a diameter substantially the same as a maximum diameter of the bulbous element.

10. An implantable medical device according to claim 1, wherein the at least one leg element is a sprung element.

11. An implantable medical device according to claim 1, wherein the at least one leg element is sprung in a radially outward direction relative to a longitudinal direction of the medical device.

12. An implantable medical device according to claim 1, including a plurality of leg elements disposed in spaced relation to one another and extending to radially outward positions.

13. An implantable medical device according to claim 1, wherein the device is a vascular filter.

14. An implantable medical device including a frame, the frame including at least one leg element having a vessel engaging end and an anchoring element at said end; wherein the anchoring element includes a bulbous element and a barb member extending from the bulbous element, wherein the barb member attached to the bulbous element; wherein the bulbous element and the barb member configured to embed within the vessel wall; wherein the barb member is made of biodegradable material, wherein the bulbous element is made of non-degradable material, and wherein the barb member is biodegradable so as to leave the bulbous element exposed within the vessel wall.

15. The implantable medical device of claim 14, wherein the bulbous element includes a barb fixation recess, the barb member including a protrusion extending into the fixation recess.

16. The implantable medical device of claim 14, wherein the barb member extends in a radially outward direction relative to a longitudinal direction of the medical device.

17. The implantable medical device of claim 14, wherein the barb member includes a base portion having a diameter substantially the same as a maximum diameter of the bulbous element.

18. The implantable medical device of claim 14, wherein the barb member extends over the bulbous element.

19. An implantable medical device including a frame, the frame including at least one leg element having a vessel engaging end and an anchoring element at said end; wherein the anchoring element includes a bulbous element and a barb member extending over the bulbous element, wherein the barb member attached to the bulbous element; wherein the bulbous element and the barb member configured to embed within the vessel wall; wherein the barb member is made of biodegradable material, wherein the bulbous element is in the form of an enlarged head, wherein the enlarged head has a fixed size and shape and does not degrade, wherein after the barb member fully degrades, the vessel engaging end will consist solely of the enlarged head portion embedded within the vessel wall.

* * * * *